(12) United States Patent
Roorda et al.

(10) Patent No.: US 8,512,388 B1
(45) Date of Patent: Aug. 20, 2013

(54) STENT DELIVERY CATHETER WITH IMPROVED STENT RETENTION AND METHOD OF MAKING SAME

(75) Inventors: Wouter Roorda, Palo Alto, CA (US); Tim A. Limon, Cupertino, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 3104 days.

(21) Appl. No.: 10/877,873

(22) Filed: Jun. 24, 2004

(51) Int. Cl.
*A61F 2/06* (2013.01)

(52) U.S. Cl.
USPC ........................................................ 623/1.11

(58) Field of Classification Search
USPC ........................................................ 623/1.11
See application file for complete search history.

(56) References Cited

U.S. PATENT DOCUMENTS

| | | | |
|---|---|---|---|
| 5,836,965 A | 11/1998 | Jendersee et al. | |
| 5,900,246 A | 5/1999 | Lambert | |
| 5,968,069 A | 10/1999 | Dusbabek et al. | |
| 5,976,155 A | 11/1999 | Foreman et al. | |
| 5,976,181 A * | 11/1999 | Whelan et al. | 623/1.12 |
| 6,063,092 A | 5/2000 | Shin et al. | |
| 6,187,013 B1 | 2/2001 | Stoltze et al. | |
| 6,203,558 B1 | 3/2001 | Dusbabek et al. | |
| 6,335,029 B1 | 1/2002 | Kamath et al. | |
| 6,562,061 B1 | 5/2003 | Wang et al. | |
| 6,569,192 B1 | 5/2003 | Svensson et al. | |
| 6,620,191 B1 | 9/2003 | Svensson | |
| 6,629,992 B2 | 10/2003 | Bigus et al. | |
| 6,666,880 B1 | 12/2003 | Chiu et al. | |
| 6,682,553 B1 | 1/2004 | Webler, Jr. | |
| 2002/0133183 A1 * | 9/2002 | Lentz et al. | 606/155 |
| 2002/0195196 A1 * | 12/2002 | Peters et al. | 156/308.6 |
| 2003/0144683 A1 | 7/2003 | Sirhan et al. | |
| 2003/0204238 A1 | 10/2003 | Tedeschi | |
| 2005/0226991 A1 * | 10/2005 | Hossainy et al. | 427/2.1 |

FOREIGN PATENT DOCUMENTS

EP 0 834 293 A1 4/1998

* cited by examiner

*Primary Examiner* — Gary Jackson
*Assistant Examiner* — L Bachman
(74) *Attorney, Agent, or Firm* — Fulwider Patton LLP

(57) ABSTRACT

A stent delivery catheter system having a catheter with stent releasably mounted on a stent retention portion of the catheter for delivery and deployment within a patient's body lumen, and a method of mounting the stent on the stent retention portion of the catheter. The method generally includes exposing the stent retention portion and/or the stent to a solvent, the solvent being in the vapor phase. The vapor phase solvent typically softens the stent retention portion of the catheter, and/or, in one embodiment in which the stent has a coating on the stent body, the vapor phase solvent softens the stent coating. In a presently preferred embodiment, the stent polymeric coating has a therapeutic agent, and the method of the invention prevents or inhibits disadvantageously affecting the therapeutic agent coating during mounting of the stent on the catheter.

25 Claims, 3 Drawing Sheets

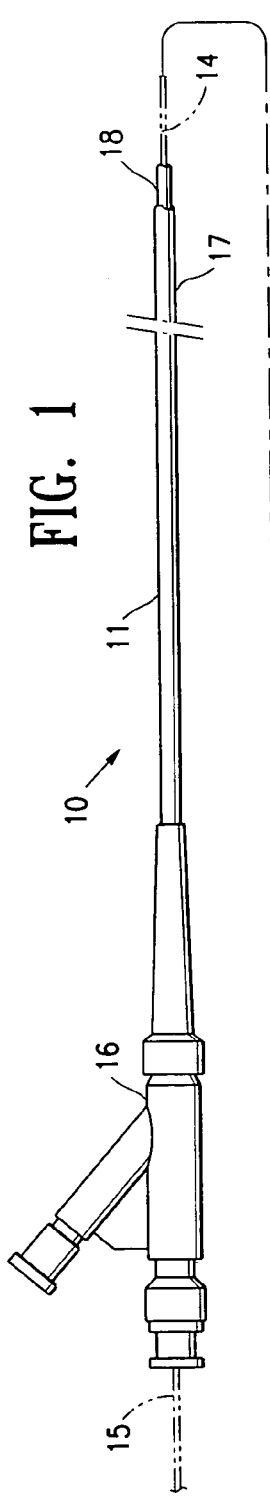
FIG. 1
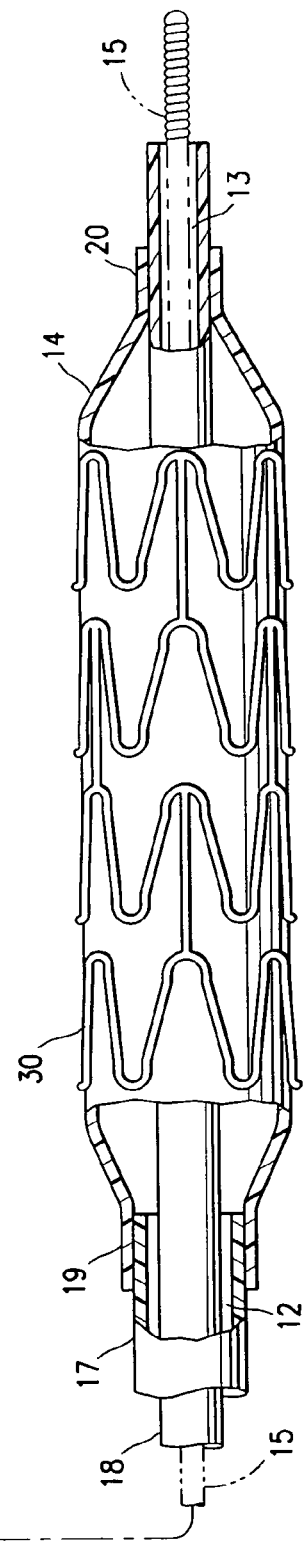
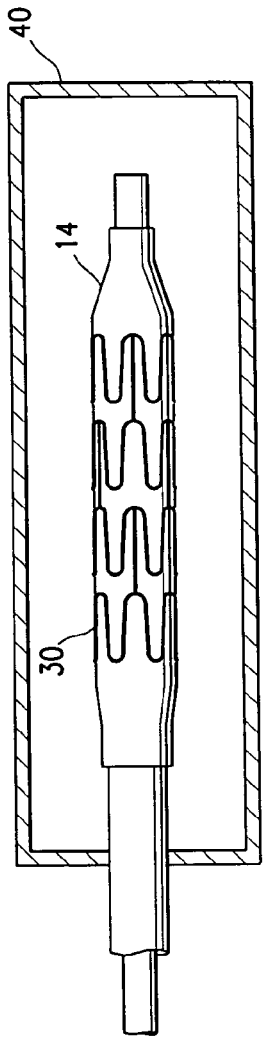
FIG. 2

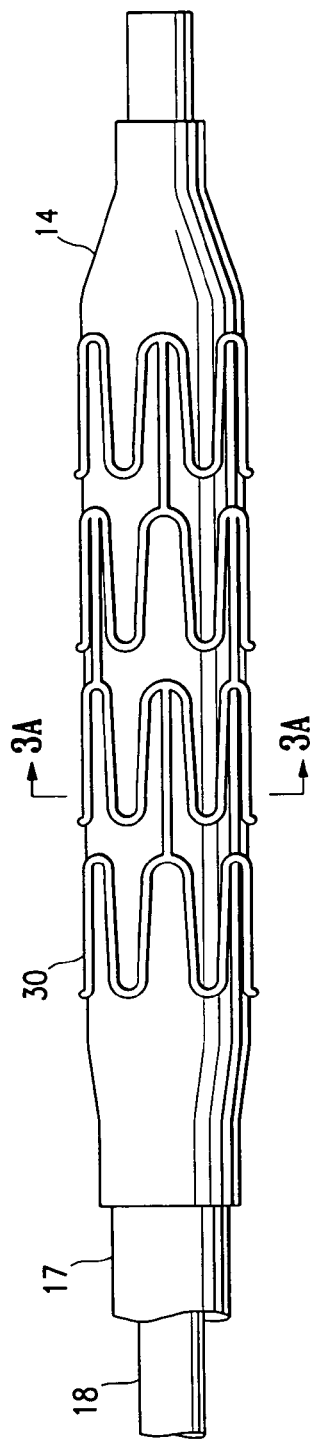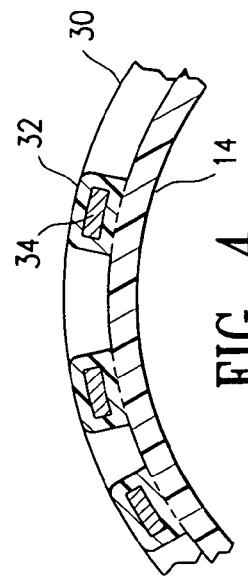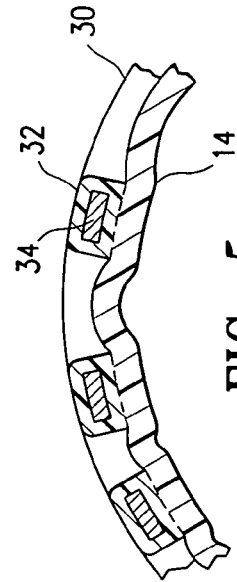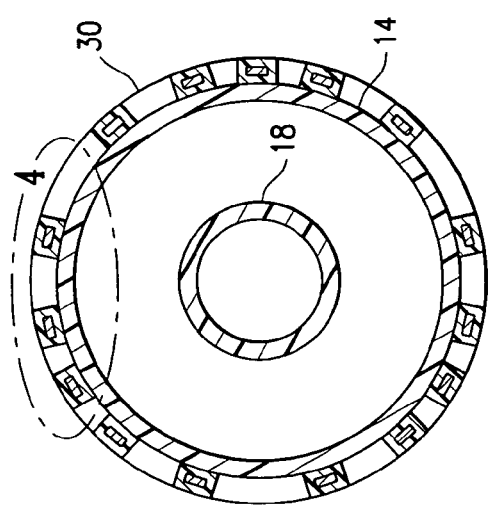

STENT DELIVERY CATHETER WITH IMPROVED STENT RETENTION AND METHOD OF MAKING SAME

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not over expand the artery wall. After the balloon is finally deflated, blood resumes through the dilated artery and the dilatation catheter and the guidewire can be removed therefrom.

In such angioplasty procedures, there may be restenosis of the artery, i.e., reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion.

One difficulty has been securely mounting the stent on the balloon catheter such that the stent remains in place on the balloon (generally referred to as "stent retention") during positioning within a patient's body lumen, without inhibiting release of the stent at the desired location in the body lumen. Additionally, mounting the stent on the balloon is more difficult if the stent or balloon has a coating, such as a drug delivery coating, which must be protected from damage during the mounting processes. Accordingly, it would be a significant advance to provide a stent delivery system with improved stent retention, without disadvantageously effecting stent release or a coating on the stent.

INVENTION SUMMARY

The invention is directed to a stent delivery catheter system having a catheter with a stent releasably mounted on a stent retention portion of the catheter for delivery and deployment within a patient's body lumen, and a method of mounting the stent on the stent retention portion of the catheter. The method generally includes exposing the stent retention portion and/or the stent to a solvent, the solvent being in the vapor phase. The vapor phase solvent typically softens the stent retention portion of the catheter, and/or, in one embodiment in which the stent has a coating on the stent body, the vapor phase solvent softens the stent coating. Softening the stent retention portion and/or stent coating facilitates releasably mounting the stent on the stent retention portion. Preferably, the softening effect of the vapor allows the balloon to be deformed during mounting of the stent on the balloon under conditions of lower pressure and/or temperature compared to the process without the solvent vapor. The method of the invention provides a stent delivery catheter with improved stent retention during advancement of the stent in the patient's body lumen, preferably without inhibiting stent release after expansion of the stent in the patient's body lumen. In a presently preferred embodiment, the stent polymeric coating has a therapeutic agent, and the method of the invention prevents or inhibits disadvantageously affecting the therapeutic agent coating during mounting of the stent on the catheter.

In one embodiment, the stent is a balloon expandable stent mounted on the balloon (i.e., stent retention portion) of a balloon catheter. In an alternative embodiment, the stent is a self-expanding stent mounted on a self-expanding stent delivery catheter. Although discussed below primarily in terms of the embodiment in which the catheter system is a balloon expandable stent mounted on a balloon catheter, it should be understood that the catheter system can be a self expanding stent system. Details regarding self-expanding stent delivery systems can be found in U.S. Pat. Nos. 6,676,693 and 6,576,006, incorporated herein by reference in their entirety.

The stent delivery balloon catheter of the invention typically comprises an elongated shaft having a proximal end, a distal end, an inflation lumen, and a guidewire lumen configured to slidably receive a guidewire therein. A balloon is secured to the shaft so that an inflatable interior of the balloon is in fluid communication with the inflation lumen.

Mounting the stent on the balloon typically comprises positioning the stent on the balloon, and forcing the balloon and stent together. Forcing the balloon and stent together can be achieved using a variety of suitable methods and should be understood to include methods in which only one of the balloon or stent are forced toward the other component. For example, mounting the stent on the balloon typically involves crimping the stent to a radially collapsed diameter on the balloon. One or more additional steps may be used to mount the stent on the balloon, typically involving pressurizing the balloon. For example, in one embodiment, mounting the stent on the balloon includes pressurizing the balloon with the stent radially constrained by a mold or sheath therearound, which forces the balloon into the spaces between adjacent struts of the stent. Similarly, there are optional steps, such as one in which the balloon is pressurized and is radially constrained by a sheath, and heat is applied to all or part of the balloon during mounting of the stent on the balloon. The softening effect of the solvent vapor may be used in any one or more of the steps used to mount the stent on the balloon. Thus, in one embodiment in which the stent is mounted on the balloon by being positioned on the balloon, then crimped on the balloon, and then pressurized to force the balloon into spaces in the stent wall, the balloon and/or stent may be exposed to the solvent vapor before, during, or after any one or more of the mounting steps. In one embodiment, the stent is positioned on the balloon, and the balloon and stent thereon are exposed to the solvent vapor prior to the stent being fully crimped onto the balloon, which preferably facilitates softening the entire surface of the balloon and/or stent coating. However, in an alternative embodiment, the balloon and/or stent are exposed to the solvent vapor during or after the stent is fully crimped onto the balloon. In one presently preferred embodiment, after the stent is crimped on the balloon, the balloon and stent are exposed to the solvent vapor during pressurization of the balloon to force the balloon into the spaces between adjacent stent struts.

Use of the softening effect of the solvent vapor in accordance with the invention preferably results in an interference fit and/or adhesion between the balloon and mounted stent. For example, in one embodiment, forcing the balloon and stent together during mounting of the stent causes portions of the softened balloon to protrude a sufficient amount into the spaces between adjacent struts of the stent to inhibit longitudinal movement of the stent mounted on the balloon. However, in an alternative embodiment, the balloon does not protrude in the mounted stent spaces, so that the stent spaces are free or substantially free of the balloon. Although discussed below primarily in terms of a system having a coated stent, it should be understood that in one embodiment the stent is not coated (e.g., a bare metal stent), and stent retention is enhanced primarily due to the portions or the balloon which are caused to protrude into the stent spaces according to a method of the invention.

The solvent vapor softens the polymeric material of the balloon and/or stent coating typically by being a temporary plasticizer of the polymer, or by temporarily swelling the polymer, depending on the nature of the solvent and the polymer. A variety of suitable solvents can be used including an organic solvent (e.g., an alcohol, acetone) or an inorganic solvent (e.g., water). For example, in one embodiment, the balloon comprises a polyamide such as nylon or a copolyamide such as PEBAX (polyether block amide) and the solvent is selected from the group consisting of water vapor, hydroxylated organic solvents (e.g., alcohols such as isopropyl alcohol), and dipolar aprotic solvents (e.g., DMSO, DMF, DMAC). In another embodiment, the balloon comprises a polyurethane and the solvent is selected from the group consisting of the hydroxylated organic solvents, the dipolar aprotic solvents, and polar organic solvents (e.g., ketones, ethers, esters, and chlorinated solvents). In another embodiment, the balloon comprises an acrylate or methacrylate and the solvent is selected from the group consisting of the dipolar aprotic solvents and the polar organic solvents. In another embodiment, the balloon comprises latex and the solvent is the dipolar aprotic solvent. In another embodiment, the balloon comprises polyethylene terephthalate (PET) and the solvent is selected from the group consisting of the hydroxylated organic solvents and the dipolar aprotic solvents. In another embodiment, the balloon comprises polyethylene and the solvent is selected from the group consisting of the polar organic solvents, and non-polar solvents (e.g., hydrocarbons, fluorocarbons, and aromatics). In another embodiment, the balloon comprises a fluoropolymer such as expanded polytetrafluoroethylene (ePTFE) and the solvent is the non-polar solvent.

In a presently preferred embodiment, the solvent is a liquid phase solvent at room temperature and pressure, although in alternative embodiments, the solvent is a solid or gas phase solvent at room temperature and pressure. In one embodiment, the method includes generating the solvent vapor, to provide a sufficiently high concentration of solvent vapor at the surface of the balloon and/or stent to soften the balloon and/or a coating on the stent.

In a presently preferred embodiment, the stent comprise a body and a polymeric coating on the body. The stent body is typically metallic although it can alternatively be non-metallic (e.g., a plastic or a bioabsorbable compound). Details regarding stents can be found for example in, U.S. Pat. No. 5,507,768 (Lau, et al.), incorporated herein by reference in its entirety. A variety of suitable coatings can be used on the stent including therapeutic, diagnostic, or lubricious coatings.

In one embodiment, the stent polymeric coating has a therapeutic agent, such as an antirestenosis agent or an antithrombosis agent. The solvent vapor softens the stent polymeric coating and/or the balloon without disadvantageously affecting the therapeutic agent polymeric coating. For example, the softening effect of the solvent vapor avoids the need for exposing the therapeutic agent coating to relatively high temperatures and pressures to soften and force the balloon and stent together during mounting of the stent on the balloon. In conventional methods of mounting a stent on a catheter balloon, the stent is mounted on the balloon with the balloon at elevated temperature and/or pressure. However, because the balloon and/or stent coating are softened by the solvent vapor in the method of the invention, the method securely mounts the stent onto the balloon while avoiding the use of high temperatures and pressures during stent mounting. Thus, in a method of the invention, the stent is mounted onto the balloon with the balloon and stent at room temperature, or at an elevated temperature lower than the elevated temperatures normally used during conventional stent mounting methods. In one embodiment in which the stent is coated with an anti-restenosis drug, the stent coating is at room temperature, or at an elevated temperature of less than about 70° C. to about 80° C., as the stent is mounted on the balloon. Similarly, in one embodiment, lower pressures are used to pressurize the balloon and radially collapse the stent onto the balloon during stent mounting in a method of the invention. Moreover, if no higher temperature or pressure can be used during stent mounting, better stent retention can be obtained at a given temperature and pressure with the solvent vapor than without the solvent vapor (including the temperatures and pressures normally used in conventional stent mounting methods) due to the softening provided by the solvent vapor.

Unlike a liquid solvent, the solvent vapor avoids the potential leaching of the therapeutic agent from the polymeric coating. Consequently, the therapeutic agent polymeric coating of the stent has a therapeutic agent concentration which is the same or substantially the same as (i.e., not more than about 0 to about 10% less than) a therapeutic agent concentration of the coated stent prior to mounting on the stent receiving portion. Similarly, in one embodiment, exposing the coating to the vapor phase solvent does not cause the therapeutic agent to migrate in the coating, so that the therapeutic agent polymeric coating of the stent mounted on the balloon has a therapeutic agent distribution which is the same or substantially the same as a therapeutic agent distribution of the coated stent prior to mounting on the balloon. Moreover, the solvent vapor preferably does not change the therapeutic agent or polymer morphology (e.g., crystalline structure) of the therapeutic agent polymeric coating, and thus avoids affecting the therapeutic agent release rate from the polymeric coating, so that the therapeutic agent polymeric coating of the stent has a therapeutic agent release rate which is the same or substantially the same as (i.e., not more than about 0 to about 25% different than) a therapeutic agent release rate of the coated stent prior to mounting on the stent receiving portion. Moreover, unlike a liquid solvent which may overwet the balloon and/or stent, the solvent vapor facilitates exposing the balloon and/or stent to small amounts of solvent over a short duration, which prevents or inhibits the solvent vapor from weakening bonded regions of the stent delivery catheter (e.g., the bonds between the balloon and the catheter shaft). Additionally, the solvent vapor easily evaporates from the balloon and/or stent, so that residual solvent does not remain behind. Thus, the method of the invention preferably avoid the potential of a liquid solvent to pool within folds and spaces of the stent delivery system. These and other advantages of the invention will become more apparent from the following detailed description and exemplary drawings.

BRIEF DESCRIPTION OF THE DRAWINGS

FIG. 1 is an elevational view, partially in section, of a stent delivery balloon catheter which embodies features of the invention having a stent mounted on the balloon.

FIG. 2 illustrates a method of mounting the stent on the balloon, with the distal end of the catheter inside a chamber for exposing the balloon and stent thereon to a solvent vapor.

FIG. 3 illustrates the distal end of the catheter after the stent is fully crimped onto the balloon.

FIG. 3A is a transverse cross sectional view of the catheter shown in FIG. 3, taken along line 3A-3A.

FIG. 4 illustrates an enlarged view of the balloon and stent of FIG. 3A within circle 4.

FIG. 5 illustrates an alternative embodiment of the catheter of FIG. 3A, having portions of the balloon wall protruding into spaces between adjacent struts of the stent.

DETAILED DESCRIPTION OF THE PREFERRED EMBODIMENTS

Figure 6:
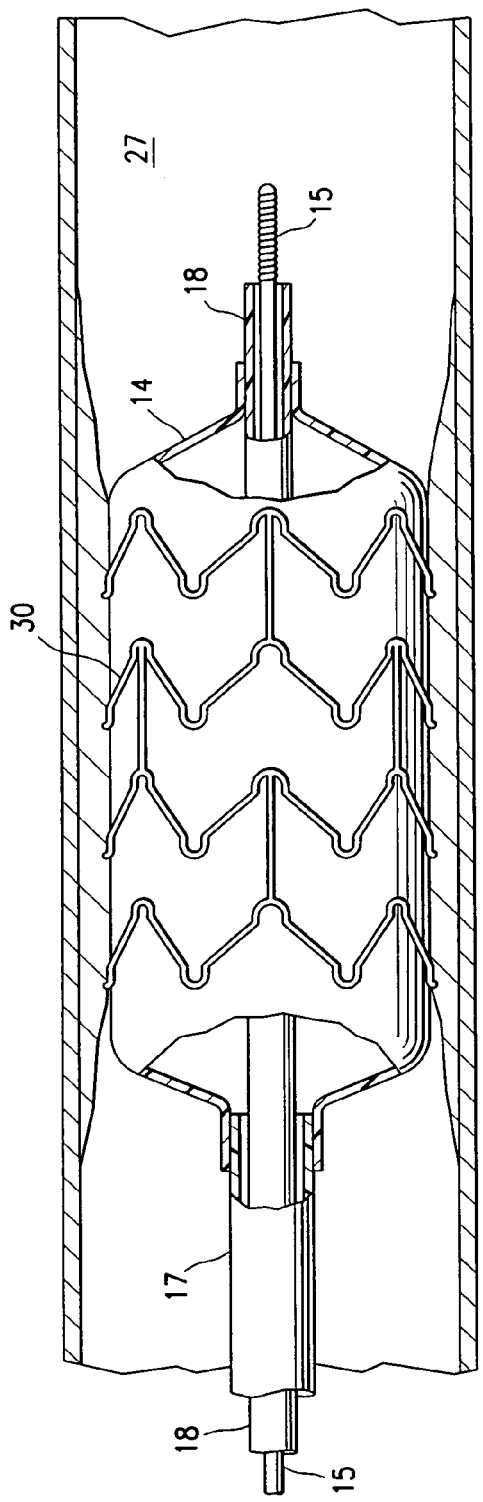
FIG. 6 illustrates the balloon catheter of FIG. 1, with the balloon inflated in a patient's body lumen to implant the stent therein.

FIG. 1 illustrates a stent delivery balloon catheter 10 embodying features of the invention, generally comprising a shaft 11 with an inflation lumen 12, and a guidewire lumen 13 configured to slidingly receive a guidewire 15, and a balloon 14 on a distal shaft section. An adapter 16 at the proximal end of catheter shaft 11 is configured to direct inflation fluid into inflation lumen 12 to thereby inflate the balloon 14, and provide access to guidewire lumen 13. FIG. 1 illustrates the balloon 14 in a low profile configuration prior to inflation, with a radially expandable stent 30 mounted on the balloon, for introduction and advancement within the patient's body lumen. In use, the distal end of catheter 10 is advanced to a desired region of the patient's body lumen in a conventional manner either over previously positioned guidewire 15, or with guidewire 15 already in the catheter 10. The balloon 14 is inflated to expand stent 30, and the balloon deflated for removal of the catheter 10 from the body lumen, leaving the stent 30 implanted in the body lumen.

In the embodiment of FIG. 1, the shaft 11 comprises an outer tubular member 17 defining the inflation lumen 12, and an inner tubular member 18 defining the guidewire lumen 13 extending from a guidewire distal port in a distal end portion of the catheter shaft to a guidewire proximal port at the proximal end of the inner tubular member 18. Inflatable balloon 14 has a proximal skirt section 19 sealingly secured to the distal end of outer tubular member 17, a distal skirt section 20 sealingly secured to the inner tubular member 18, and an inflatable cylindrical working length section therebetween, so that its interior is in fluid communication with inflation lumen 12.

The stent 30 is mounted onto the balloon according to a method which embodies features of the invention in which the balloon and/or a coating on the body of the stent are softened by being exposed to a solvent vapor. The balloon 14 and/or stent 30 may be exposed to the solvent vapor during, before, or after any of the steps used to mount the stent onto the balloon. In a presently preferred embodiment, the balloon and/or stent coating are in the softened condition during pressurization of the balloon to force the balloon into spaces in the wall of the stent. Specifically, during mounting of the stent on the balloon, the subassembly of the stent on the balloon typically has a restraining member such as a mold or sheath therearound, and the balloon is pressurized which forces the balloon and stent together. The balloon is pressurized by directing an inflation medium into the interior of the balloon, and the pressure within the balloon typically reaches pressures within or above the working pressure range of the balloon, such as about 14 atm, due to the restraining member therearound.

The balloon and/or stent coating may additionally or alternatively be in the softened condition during crimping of the stent on the balloon. FIG. 2 illustrates the distal end of the balloon catheter 10 with the stent 30 positioned on the balloon 14, within a chamber 40 for exposure to solvent vapor in the chamber 40. The stent 30 is typically radially collapsed to a pre-crimped intermediate diameter to position it securely on the balloon 14. In one embodiment, following exposure to the solvent vapor, the pre-crimped stent is then further radially collapsed to a crimped diameter. A variety of suitable devices can be used as the chamber 40, including the crimping equipment used to crimp the stent 30 on the balloon 14, or other pieces of equipment normally used during catheter assembly. Alternatively, the chamber 40 can be a separate container not normally used during catheter assembly. Thus, in one embodiment, after exposure to the solvent vapor in the chamber 40, the catheter 10 and stent 30 positioned thereon are moved from the chamber 40 to the crimping equipment to fully crimp the stent 30 onto the balloon 14.

Generally, a sufficient amount of solvent vapor to soften the balloon and/or stent coating is typically at least about 1% of atmospheric pressure, corresponding to a solvent vapor pressure of at least about 7.6 Torr. In one embodiment, the liquid solvent, has a sufficiently high vapor pressure at ambient temperature and pressure to provide a sufficient amount of solvent vapor to soften the balloon and/or stent coating. For example, fluorocarbons and low-boiling polar organic solvents typically provide sufficient solvent vapor without being heated. However, higher boiling solvents would required heating to generate sufficient vapor. Thus, in one embodiment, the method of the invention involves heating a liquid or solid solvent to provide a sufficient amount of solvent vapor to soften the balloon, or at least to increase the solvent vapor pressure. For example, in one embodiment in which the solvent is water, the solvent is vaporized, so that the solvent vapor is steam. In one embodiment in which the chamber 40 is also the crimping equipment used to crimp the stent onto the balloon, a reservoir of the solvent is provided in the chamber 40, and the solvent in the reservoir is heated to an elevated temperature at which sufficient vapor is generated locally within the chamber 40. Another suitable method that is less dependent on temperature would be to pass an inert gas, such as nitrogen or argon, through a reservoir of the solvent, and then pass this saturated vapor stream past the balloon and/or stent coating.

Following exposure to the solvent vapor, the solvent is allowed to evaporate from the exposed balloon and stent thereon. The balloon with the stent thereon can be dried to quicken evaporation of the solvent. However, depending on the conditions of operation and the solvent used, the solvent may flash off quickly from the exposed balloon and stent without heating or otherwise drying the balloon and stent.

FIG. 3 illustrates the distal end of the catheter 10 of FIG. 2 after the stent 30 is mounted onto balloon 14 for delivery and deployment within a patient's body lumen. FIG. 3A illustrates a transverse cross sectional view of the stent delivery system of FIG. 3 taken along line 3A-3A. FIG. 4 illustrates an enlarged view of the balloon 14 and stent 30 of FIG. 3A taken within circle 4. In one embodiment, the stent 30 comprises a body 32 and a polymeric coating 34 on the body. The stent body 32 is typically metallic, and typically comprises a radially expandable tubular structure of interconnected spaced-apart struts, as is conventionally known in the design of stents. In accordance with one embodiment of the invention, with the stent mounted on the uninflated balloon 14, the balloon 14 and stent coating 34 are releasably adhered together. Specifically, at least one of the balloon 14 and stent coating 34 are temporarily softened by the solvent vapor so that they releasably adhere together when in contact as the solvent evaporates therefrom. As illustrated in FIG. 4, an inner surface of the fully crimped stent 30 is in contact with an outer surface of the balloon 14. The outer surface of the balloon 14 is releasably adhered directly to the inner surface of the stent 30 (i.e., a separate adhesive is not provided between the stent and balloon surface). In one embodiment, in order to prevent or inhibit damaging the adhesion between the balloon and stent during the crimping process, the stent is fully crimped onto the balloon in the temporarily softened condition before the surfaces become releasably adhered together. In a presently preferred embodiment, the section of the balloon under the stent mounted thereon does not have a lubricious coating. Thus, the polymeric material forming the inflatable wall of the balloon defines the outer surface of the balloon. However, in an alternative embodiment, the section of the balloon under the stent does have a lubricious coating, and exposing the balloon to the vapor phase solvent softens the material forming the lubricious coating of the balloon and/or the polymeric material forming the inflatable wall of the balloon.

In one embodiment, the stent coating has a therapeutic agent and the therapeutic agent polymeric coating 34 defines the stent inner surface releasably adhered to the balloon outer surface. Alternatively, in one embodiment, a release rate limiting top coat (not shown) is on the outer surface of the therapeutic agent polymeric coating 34. The therapeutic agent polymeric coating 34 typically has the therapeutic agent dispersed throughout the coating 34 although it can alternatively be on a surface of the coating 34 or otherwise limited to a portion of the coating 34. A variety of suitable polymers can be used for polymeric coating 34, including acrylates, methacrylates, poly(vinylidene fluoride), poly(vinylidene fluoride-co-hexafluoropropene), fluorocarbons, vinyl-based polymers, silicone-urethanes, polyurethanes, ethylene vinyl acetate, poly(ethylene-co-vinyl alcohol), styrene-isobutylene-styrene triblock copolymers, styrene-ethylene/butane-styrene triblock copolymers, silicones, polymers functionalized with active groups like heparin or with biomimetic compounds, poly-esters, bioerodible as well as biostable compounds, and any other polymers, copolymers or polymer combinations with acceptable vascular biocompatibility. The polymeric coating 34 can be applied to the stent body by a variety of suitable means including, dipping, spraying, wiping, and depositing.

In the embodiment of FIG. 4, the uninflated balloon wall has a flat outer surface which does not protrude into the spaces between adjacent stent body struts 32. In an alternative embodiment illustrated in FIG. 5, portions of the wall of the uninflated balloon 14 protrude in the spaces between adjacent struts of the mounted stent. In the embodiment illustrated in FIG. 5, the protrusions extend into the spaces such that less than half of the width of the wall of the stent is occupied by the protrusions. However, it should be understood that in alternative embodiments (not shown) the protrusions extend into the spaces in the stent wall an amount which is greater or lesser than the amount illustrated in FIG. 5. Temporarily softening the balloon 14 by exposure to the solvent vapor facilitates forcing portions of the balloon into the spaces between the stent body struts 32. Thus, the otherwise smooth surface of the balloon 14 (i.e., it is not preformed with protrusions prior to the mounting of the stent thereon), forms protrusions extending in the wall of the mounted stent which enhance stent retention by providing resistance to longitudinal displacement of the stent mounted on the balloon. Additionally, in one embodiment, the balloon protruding into the stent spaces is releasably adhered to the stent coating 34, as discussed above in relation to the embodiment of FIG. 4. Although FIG. 5 illustrates the stent 30 with a coating 34 on the stent body 32, it should be understood that a non-coated stent 30 can alternatively be used, with the enhanced stent retention being provided by the interference caused by the balloon wall protruding into the stent wall.

FIG. 6 illustrates the balloon catheter 10 of FIG. 1 with the balloon 14 fully inflated in a patient's body lumen 27. The balloon 14 is inflated to an inflated condition at a pressure within a working pressure range of the balloon, typically about 5 to about 20 atm, so that the balloon cylindrical working section expands the stent 30 to an expanded diameter. In the embodiment in which the balloon and stent coating are adhered together, the adhesion between the balloon and stent coating preferably fails as the balloon inflates to the inflated condition within the working pressure range, so that the balloon in the inflated condition is not adhered to the expanded stent. Similarly, in the embodiment in which the balloon protrudes into the spaces in the stent wall, the protrusions are typically not a permanent feature of the balloon, so that the expanded balloon typically does not protrude into the spaces in the stent wall. Thus, the balloon can be deflated to retract radially away from the expanded stent, leaving the expanded stent 30 implanted in the body lumen.

Figure 7:
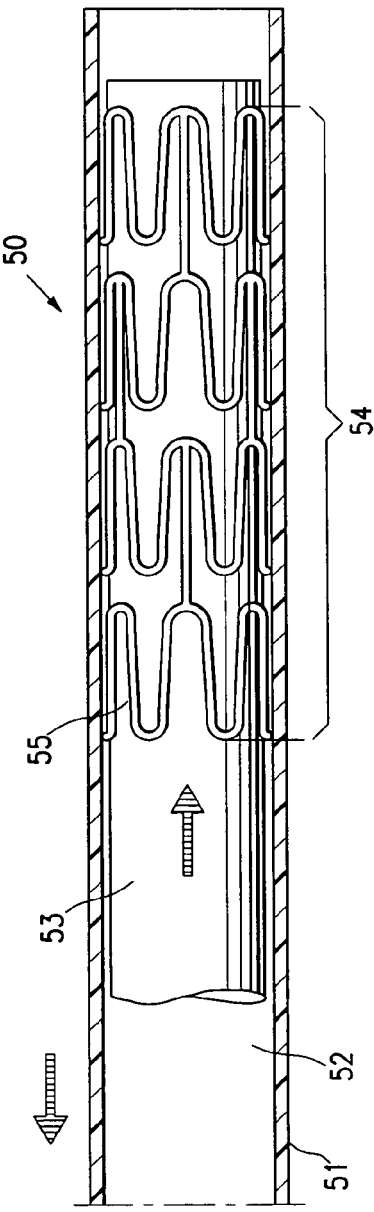
FIG. 7 illustrates a self-expanding stent delivery system embodying features of the invention.

FIG. 7 illustrates a self-expanding stent delivery system 50 embodying features of the invention. The catheter 50 comprises an outer tubular member 51 having a lumen 52 therein, and an inner tubular member 53 having a stent receiving portion 54 with an unexpanded self-expanding stent 55 mounted thereon. The inner tubular member 53 and outer tubular member 51 typically extend from the proximal to the distal end of the catheter, allowing the distal end of the inner tubular member 53 to be displaced distally out the distal end of the outer tubular member 51 when the stent receiving portion 54 is in the desired position within the patient's body lumen. The stent expands as the outer and inner tubular members 51, 53 are moved relative to one another to advance the inner tubular member 53 out the distal end of the outer tubular member 51 and thereby remove a radially restraining force from around the stent 55. The stent receiving portion 54 and/or stent are exposed to solvent vapor in accordance with the invention during mounting of the stent 55 on the stent receiving portion 54.

To the extent not previously discussed herein, the various catheter 10, 50 components may be formed and joined by conventional materials and methods. The inner and outer tubular members can be formed by conventional techniques, such as by extruding and necking materials found useful in intravascular catheters such as polyethylene, polyvinyl chloride, polyesters, polyamide, polyimides, polyurethanes, and composite materials. The balloon can be formed by a variety of conventional methods including blow molding or otherwise forming an inflatable tubular member from conventional balloon materials such as polyamide (nylon), PEBAX, and polyurethane.

The length of the balloon catheter 10, 50 is generally about 137 to about 145 centimeters, and typically about 140 centimeters for PTCA. The outer tubular member has an OD of about 0.017 to about 0.034 inch (0.43-0.87 mm), and an inner diameter (ID) of about 0.017 to about 0.026 inch (0.43-0.66 mm). The inner tubular member has an OD of about 0.015 to about 0.022 inch (0.38-0.56 mm), and an ID of about 0.012 to about 0.018 inch (0.30-0.46 mm) depending on the diameter of the guidewire to be used with the catheter. The balloon 14 is typically about 8 to about 38 mm in length, with an inflated working diameter of about 1.5 to about 5 mm.

While the present invention has been described herein in terms of certain preferred embodiments, those skilled in the art will recognize that modifications and improvements may be made without departing from the scope of the invention. For example, although the catheter illustrated in FIG. 1 is an over-the-wire type balloon catheter, a variety of suitable catheter designs can be used including rapid exchange type catheters. Rapid exchange type catheters generally comprise a distal guidewire port in a distal end of the catheter, a proximal guidewire port in a distal shaft section and typically spaced a substantial distance from the proximal end of the catheter, and a relatively short guidewire lumen extending between the proximal and distal guidewire ports. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

We claim:

1. A method of mounting a stent on a stent delivery balloon catheter, comprising:
    a. softening a catheter balloon to a softened condition by exposing the balloon to a solvent, the solvent being in the vapor phase; and
    b. applying a force urging the balloon and a stent on the balloon together, with the balloon in the softened condition, to mount the stent on the balloon.

2. The method of claim 1 wherein applying the force urging the balloon and stent together comprises radially collapsing the stent onto the balloon.

3. The method of claim 1 wherein applying the force urging the balloon and stent together comprises pressurizing the balloon.

4. The method of claim 1 wherein the stent comprises a body and a polymeric coating on the body, and including, before or during b), exposing the stent polymeric coating to the vapor phase solvent, to thereby soften the stent polymeric coating.

5. The method of claim 4 including, after b), allowing the solvent to evaporate from the balloon and stent polymeric coating, so that the mounted stent is releasably adhered to the balloon.

6. The method of claim 4 wherein the stent comprises interconnected spaced-apart struts, and including forcing the balloon in the softened condition within the space between adjacent struts, so that the mounted stent has portions of the balloon protruding in the space between adjacent struts.

7. The method of claim 4 wherein the stent polymeric coating has a therapeutic agent, and exposing the coating to the vapor phase solvent does not remove the therapeutic agent from the coating, so that the therapeutic agent polymeric coating of the stent mounted on the balloon has a therapeutic agent concentration which is the same or substantially the same as a therapeutic agent concentration of the coated stent prior to mounting on the balloon.

8. The method of claim 4 wherein the stent polymeric coating has a therapeutic agent, and exposing the coating to the vapor phase solvent does not cause the therapeutic agent to migrate in the coating, so that the therapeutic agent polymeric coating of the stent mounted on the balloon has a therapeutic agent distribution which is the same or substantially the same as a therapeutic agent distribution of the coated stent prior to mounting on the balloon.

9. The method of claim 4 wherein the stent polymeric coating has a therapeutic agent, and b) comprises applying the force urging the balloon and stent together with the stent and balloon at room temperature.

10. The method of claim 4 wherein the stent polymeric coating has a therapeutic agent, and b) comprises applying the force urging the balloon and stent together with the stent and balloon at a temperature of less than about 70° C. to about 80° C.

11. A method of mounting a stent on a stent delivery catheter, comprising:
    a. positioning a stent on a catheter balloon, the stent comprising a body and a polymeric coating on the body;
    b. exposing the balloon and stent to a solvent, the solvent being in the vapor phase; and
    c. allowing the solvent to evaporate from the balloon and stent polymeric coating, so that the balloon and stent releasably adhere together.

12. The method of claim 11 wherein exposing the balloon and stent to the vapor phase solvent softens at least one of the balloon and the stent polymeric coating to a softened condition.

13. The method of claim 11 wherein b) includes heating the solvent to increase the vapor pressure of the solvent.

14. The method of claim 11 wherein b) includes vaporizing or subliming the solvent.

15. The method of claim 11 wherein the solvent is an inorganic solvent, and b) includes generating the inorganic solvent vapor by heating the inorganic solvent or saturating a vapor stream past through a liquid sample of the inorganic solvent.

16. The method of claim 11 wherein the solvent is an organic solvent, and b) includes generating the organic solvent vapor by heating the organic solvent or saturating a vapor stream past through a liquid sample of the organic solvent.

17. The method of claim 16 wherein the organic solvent is selected from the group consisting of an alcohol and acetone.

18. The method of claim 11 wherein the stent polymeric coating has a therapeutic agent, and a) comprises radially collapsing the stent to a pre-crimped intermediate diameter, and b) comprises exposing the balloon and stent to the solvent vapor with the stent in the pre-crimped intermediate diameter.

19. The method of claim 11 including radially collapsing the stent to a crimped diameter on the balloon after exposing the balloon and stent to the solvent vapor.

20. The method of claim 11 including radially collapsing the stent to a crimped diameter on the balloon before exposing the balloon and stent to the solvent vapor.

21. The method of claim 11 including pressurizing the balloon in the softened condition.

22. The method of claim 11 wherein the stent comprises interconnected spaced-apart struts, and including forcing the balloon in the softened condition within the space between adjacent struts, so that the mounted stent has portions of the balloon protruding in the space between adjacent struts.

23. A method of mounting a stent on a stent delivery catheter, comprising:
   a. positioning a stent on a stent receiving portion of a stent delivery catheter, the stent comprising a body and a polymeric coating on the body; and
   b. exposing the stent receiving portion and stent thereon to a solvent, the solvent being in the vapor phase, to thereby soften at least one of the stent receiving portion and the stent polymeric coating.

24. The method of claim 23 wherein the stent is a self-expanding stent and including radially collapsing the stent on the stent receiving portion of the stent delivery catheter.

25. The method of claim 23 wherein the stent receiving portion of the stent delivery catheter is a balloon, and including radially collapsing the stent on the balloon.

* * * * *